United States Patent [19]

Hirayama et al.

[11] Patent Number: 5,017,518

[45] Date of Patent: May 21, 1991

[54] PROCESS FOR PRODUCING CALCIUM PHOSPHATE CERAMICS HAVING POROUS SURFACE

[75] Inventors: Yasuhiko Hirayama; Tetsuro Ogawa; Satoshi Ojima, all of Tokyo, Japan

[73] Assignee: Asahi Kogaku Kogyo K.K., Tokyo, Japan

[21] Appl. No.: 511,814

[22] Filed: Apr. 18, 1990

Related U.S. Application Data

[63] Continuation of Ser. No. 243,543, Sep. 13, 1988, abandoned.

[30] Foreign Application Priority Data

Sep. 14, 1987 [JP] Japan .................................. 62-230747

[51] Int. Cl.$^5$ ........................ C04B 35/00; C04B 38/04
[52] U.S. Cl. ............................................ 501/1; 501/80; 501/123; 106/35
[58] Field of Search ................ 501/1, 123, 80; 106/35

[56] References Cited

U.S. PATENT DOCUMENTS

| | | |
|---|---|---|
| 3,929,971 | 12/1975 | Roy .......................................... 501/1 |
| 4,207,306 | 6/1980 | Jarcho ..................................... 501/1 |
| 4,308,064 | 12/1981 | Takami et al. ........................... 501/1 |
| 4,371,484 | 2/1983 | Inukai et al. ............................. 501/1 |
| 4,626,392 | 12/1986 | Kondo et al. ............................ 501/1 |
| 4,693,986 | 9/1987 | Vit et al. .................................. 501/1 |

FOREIGN PATENT DOCUMENTS

| | | | |
|---|---|---|---|
| 58-083605 | 5/1983 | Japan ..................................... | 106/35 |
| 59-182263 | 10/1984 | Japan ..................................... | 106/35 |
| 62-153204 | 7/1987 | Japan ..................................... | 106/35 |

Primary Examiner—William R. Dixon, Jr.
Assistant Examiner—Anthony J. Green
Attorney, Agent, or Firm—Sughrue, Mion, Zinn Macpeak & Seas

[57] ABSTRACT

A process for producing calcium phosphate ceramics having a porous surface is described, which comprise the steps of:

a) preparing untreated calcium phosphate ceramics, which comprises a mixture of hydroxyapatite and tricalcium phosphate, and b) treating said untreated ceramics with an acidic solution to selectively dissolve the tricalcium phosphate in the surface of the ceramics.

7 Claims, 1 Drawing Sheet

PROCESS FOR PRODUCING CALCIUM PHOSPHATE CERAMICS HAVING POROUS SURFACE

This is a continuation of application Ser. No. 07/243,543, filed Sept. 13, 1988, now abandoned.

FIELD OF THE INVENTION

The present invention relates to a process for producing calcium phosphate ceramics having a porous surface.

BACKGROUND OF THE INVENTION

Recently, calcium phosphate based ceramics have increased their use as artificial teeth implants, artificial bones, etc., since they have an excellent affinity to the living body.

In the application of calcium phosphate ceramics to a living body as teeth implants, artificial bones, and the like, it is known that the affinity is much improved by increasing surface porosity and thus promoting the circulation of the humor.

Accordingly, various production processes for porous calcium phosphate ceramics are suggested. Usually employed processes are as follows:

(1) A slurry of calcium phosphate based compound is foamed by adding a foaming agent, molded to a predetermined shape, dried, and fired (as described in "Sintered hydroxyapatite as a bioceramics", Philips tech. Rev., vol. 37, pp 234-236, 1977, No. 9/10);

(2) A powder of calcium phosphate based compound is mixed with a pyrolytic organic substance, molded, pre-calcined, and fired (as described in JP-A-62-22632) (The term "JP-A" as used herein means an "unexamined published Japanese patent application").

However, the aforesaid processes tend to be complicated since they include foaming with foaming agents or mixing with pyrolytic organic matter. Moreover, the strengths of the porous ceramics are considerably low as compared with non-porous ceramics, since they are wholly composed of porous material from the inside to the surface.

SUMMARY OF THE INVENTION

An object of the present invention is to provide a process for producing strong calcium phosphate ceramics having a porous surface, by a simple process for introducing pores in the surface of untreated calcium phosphate ceramics.

Another object of the present invention is to provide a process for producing calcium phosphate ceramics having an excellent affinity to a living body.

Other objects and effects of the present invention will be apparent from the following description.

The above objects of the present invention are attained by a process for producing calcium phosphate ceramics having a porous surface which comprises the steps of:

a) preparing untreated calcium phosphate ceramics, which comprise a mixture of hydroxyapatite and tricalcium phosphate, and b) treating said untreated ceramics with an acidic solution to selectively dissolve the tricalcium phosphate in the surface of the ceramics.

DETAILED DESCRIPTION OF THE INVENTION

Figure 1:
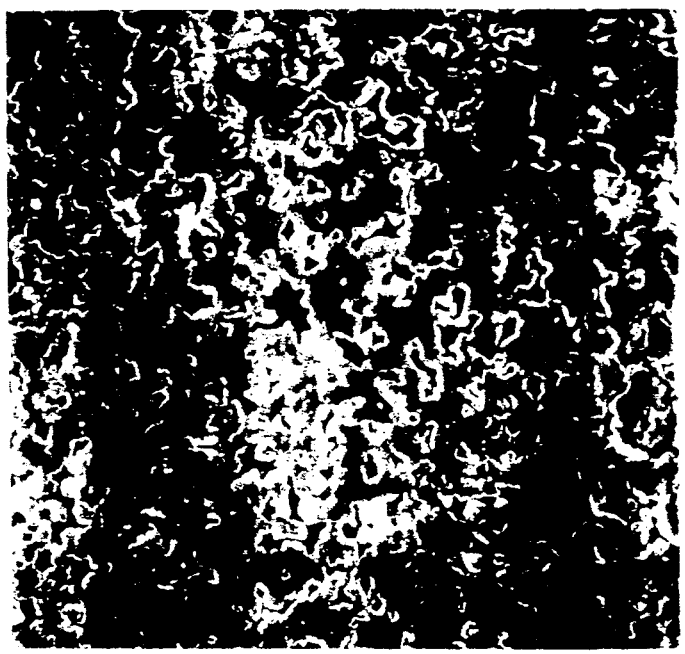
FIG. 1 is the micrograph under the magnification of 1,000 showing the surface texture of the calcium phosphate ceramics having a porous surface produced according to the present invention.

It is known that calcium phosphate ceramics are apt to dissolve in acids. The solubility differs from one sample to another, and the solubility of tricalcium phosphate ($Ca_3(PO_4)_2$) is greater than that of hydroxyapatite ($Ca_{10}(PO_4)_6(OH)_2$). The present invention is based on this knowledge and utilizes the difference in solubility between tricalcium phosphate and hydroxyapatite. That is, untreated calcium phosphate ceramics comprising a mixture of hydroxyapatite and tricalcium phosphate are treated with an acidic solution to selectively dissolve tricalcium phosphate in the surface. Thus, a porous surface is obtained by means of a simple process.

The calcium phosphate ceramics of the present invention, when used as artificial teeth implants and artificial bones, show excellent vital affinity, and this affinity is ascribed to the porous surface obtained by means of the process of the present invention. In addition, after undergoing this process, the subject ceramics maintain sufficient strength since their inner density is maintained.

In one embodiment of the present invention, a powder mixture of hydroxyapatite and tricalcium phosphate is molded as desired, pre-calcined if needed, and fired to give untreated calcium phosphate ceramics.

Known dry- and wet-synthesis processes can be employed for the synthesis of hydroxyapatite and tricalcium phosphate which are used as the starting materials. In the wet process, phosphoric acid and/or its calcium salt is brought into reaction with a calcium compound in water. It is possible to control the composition of the untreated product by adjusting the Ca/P molar ratio of the starting material to obtain a product as desired, e.g., an untreated product mainly comprising either hydroxyapatite or tricalcium phosphate, a mixture of hydroxyapatite and tricalcium phosphate, etc. The wet process is described, e.g., in Wallaeys, R.,. *Ann. Chim. (Paris)*, vol. 7, 808 and 823 (1952); Moreno, E. C., Gregory, T. M., Brown, W. E., *J. Res. Nat. Bur. Stand.*, vol. 72A, 773 (1968); and L. C. Bell, H. Mika, B. J. Kruger, *Archs. Oral. Biol.*, vol. 23, 329 to 336 (1978). The dry process is described, e.g., in Quinaux, N., *Arch. Intern. Physiol. Biochim.*, vol. 72, 337 (1964) and *Chem. Abstr.*, vol. 60, 15418a (1964); and Liteanu, C., Macarouci, D., *Studii Cercetari Chim.*, vol. 13, 157 (1962).

In the present invention, hydroxyapatite and tricalcium phosphate may be synthesized either separately or at the same time. When the synthesis is performed separately, the powders of hydroxyapatite and tricalcium phosphate are mixed thereafter. When the synthesis is simultaneous, a mixture is obtained by the wet-process, and may be further pulverized if needed. The mixture of hydroxyapatite and tricalcium phosphate preferably contains from about 20 to 80% of a tricalcium phosphate phase, that is, to give a Ca/P molar ratio in the range of from 1.53/1 to 1.64/1, more preferably from 1.57/1 to 1.64/1. In principle, it is possible to apply the present invention in the whole range of concentration ratios, provided that both hydroxyapatite and tricalcium phosphate are present. The porosity of the final product becomes higher for starting materials containing a larger amount of tricalcium phosphate.

After synthesis, the mixture of hydroxyapatite and tricalcium phosphate is then molded as desired by pressurized molding, cast molding, etc. Granules can be obtained by applying various granularization methods. In this case, binders such as water and organic solvents may be added. The thus obtained moldings are pre-calcined if needed, and then fired. The firing temperature for the present invention is preferably in the range of from 700° to 1,400° C., more preferably from 1,000° to 1,300° C. In this process, the pore diameter is larger for the samples fired at higher temperatures, since the grain growth is promoted with increasing temperature, thus leaving larger pores after the acid treatment.

The porosity of the porous surface of the calcium phosphate ceramics of the present invention is preferably from 20 to 60%. The porosity can be controlled by changing the amount or proportion of tricalcium phosphate in the untreated calcium phosphate ceramics or by changing the contact time of the untreated ceramics with the acidic solution. However, the porosity is controlled preferably by changing the amount or proportion of tricalcium phosphate.

Hydrochloric acid, nitric acid, sulfuric acid, and the like are suitably used as the acidic solution, but the acidic solution is not limited thereto. The acidic solution should preferably have a pH in the range of from 1 to 5.5. When the pH is lower than 1, hydroxyapatite dissolves, and when the pH is higher than 5.5, tricalcium phosphate is not dissolved effectively enough to produce a porous surface. The contact time with the acidic solution differs according to the acid concentration, however, 1 second to 24 hours is appropriate for a normal case.

The calcium phosphate ceramics of the present invention, having a porous surface, are suitably used for implant materials such as artificial tooth roots and artificial bones, and also for column fillers used for the separation of biopolymers.

The present invention will be described in more detail by referring the following example, but is not to be construed as being limited thereto. All ratios, parts, percents, etc. are by weight unless otherwise indicated.

EXAMPLE

Powders of hydroxyapatite and tricalcium phosphate prepared by known wet-synthetic processes were mixed to give a powder mixture having a Ca/P molar ratio of 1.55/1. The mixture was shaped in a metal mold, and fired at 1,200° C. for 4 hours to provide untreated calcium phosphate ceramics.

The above untreated calcium phosphate ceramics were immersed in an aqueous hydrochloric acid solution of pH 3 at room temperature for 10 seconds, and then drawn out from the solution. This immersion produced ceramics having a porous surface, the porous surface showing a fine irregularity ascribed to the selective dissolution of tricalcium phosphate.

FIG. 1 shows a micrograph of the treated calcium phosphate ceramics taken under the magnification of 1,000 times. The micrograph reveals a surface having fine pores. The pore diameter was in the range of 500 Å to 20 μm.

As stated in the foregoing, the present invention can provide an extremely simple process for producing calcium phosphate ceramics having a porous surface. This process comprises treating calcium phosphate ceramics comprising a mixture of hydroxyapatite and tricalcium phosphate with an acidic solution to selectively dissolve the tricalcium phosphate in the surface. The treated calcium phosphate ceramics of the present invention, having a porous surface, are suitably used for implant materials such as artificial tooth-roots and artificial bones, and also for column fillers used for the separation of biopolymers with increased affinity to a living body.

While the invention has been described in detail and with reference to specific embodiments thereof, it will be apparent to one skilled in the art that various changes and modifications can be made therein without departing from the spirit and scope thereof.

What is claimed is:

1. A process for producing calcium phosphate ceramics having a porous surface, comprising the steps of:
   a) preparing untreated calcium phosphate ceramics, said untreated ceramics comprising a mixture of hydroxyapatite and tricalcium phosphate;
   b) molding said untreated ceramics;
   c) firing said untreated ceramics; and
   d) contacting said untreated ceramics with an acidic solution to selectively dissolve the tricalcium phosphate in the surface of the ceramics but not selectively dissolve said hydroxyapatite;
   wherein the pH of the acidic solution is from 1 to 5.5.

2. A process for producing calcium phosphate ceramics having a porous surface as claimed in claim 1, wherein the mixture of hydroxyapatite and tricalcium phosphate is controlled to give a calcium to phosphorus molar ratio (Ca/P) in the range from 1.53/1 to 1.64/1.

3. A process for producing calcium phosphate ceramics having a porous surface as claimed in claim 2, wherein the mixture of hydroxyapatite and tricalcium phosphate is controlled to give a calcium to phosphorus molar ratio (Ca/P) in the range from 1.57/1 to 1.64/1.

4. A process for producing calcium phosphate ceramics having a porous surface as claimed in claim 1, wherein the firing is at a temperature of from 700° to 1,400° C.

5. A process for producing calcium phosphate ceramics having a porous surface as claimed in claim 4, wherein the firing is at a temperature of from 1,000° to 1,300° C.

6. A process for producing calcium phosphate ceramics having a porous surface according to claim 8, wherein said step of contacting untreated ceramic with an acidic solution is performed for a time period of from 1 second to 24 hours.

7. Calcium phosphate based ceramics having a porous surface produced by the process comprising the steps of:
   a) preparing untreated calcium phosphate ceramics, said untreated ceramics comprising a mixture of hydroxyapatite and tricalcium phosphate;
   b) molding said untreated ceramics;
   c) firing said untreated ceramics; and
   d) contacting said untreated ceramics with an acidic solution to selectively dissolve the tricalcium phosphate in the surface of the ceramics but not selectively dissolve said hydroxyapatite so that the inner density of said ceramics is maintained;
   wherein the pH of the acidic solution is from 1 to 5.5.

* * * * *